(12) United States Patent  
Bernabei

(10) Patent No.: US 6,743,215 B2
(45) Date of Patent: Jun. 1, 2004

(54) METHOD AND APPARATUS FOR SKIN ABSORPTION ENHANCEMENT AND CELLULITE REDUCTION

(75) Inventor: Gian Franco Bernabei, Florence (IT)

(73) Assignee: Mattioli Engineering Ltd. (GB)

( * ) Notice: Subject to any disclaimer, the term of this patent is extended or adjusted under 35 U.S.C. 154(b) by 68 days.

(21) Appl. No.: 10/074,234

(22) Filed: Feb. 14, 2002

(65) Prior Publication Data

US 2002/0147467 A1 Oct. 10, 2002

Related U.S. Application Data

(63) Continuation-in-part of application No. 09/942,044, filed on Aug. 30, 2001, which is a continuation-in-part of application No. 09/922,927, filed on Aug. 7, 2001, now Pat. No. 6,535,761.
(60) Provisional application No. 60/281,808, filed on Apr. 6, 2001.

(51) Int. Cl.[7] .............................................. A61M 31/00
(52) U.S. Cl. ..................... 604/500; 604/20; 604/22; 604/540; 601/17
(58) Field of Search ................. 604/500, 902, 604/20, 22, 540, 118; 601/15, 17, 21, 46; 607/3

(56) References Cited

U.S. PATENT DOCUMENTS

| 4,907,601 | A |   | 3/1990  | Frick |              |
|-----------|---|---|---------|-------|--------------|
| 5,538,503 | A |   | 7/1996  | Henley |             |
| 5,658,247 | A |   | 8/1997  | Henley |             |
| 5,667,487 | A |   | 9/1997  | Henley |             |
| 5,778,894 | A | * | 7/1998  | Dorogi et al. | 128/898 |
| 6,009,345 | A |   | 12/1999 | Hofmann |            |
| 6,302,874 | B1 | * | 10/2001 | Zhang et al. | 604/522 |
| 6,334,074 | B1 | * | 12/2001 | Spertell | 607/101 |
| 6,379,324 | B1 | * | 4/2002  | Gartstein et al. | 604/22 |
| 6,398,753 | B2 | * | 6/2002  | McDaniel | 604/22 |
| 6,424,862 | B1 |   | 7/2002  | Brown, III et al. | |
| 6,443,914 | B1 | * | 9/2002  | Costantino | 601/2 |
| 6,517,499 | B1 | * | 2/2003  | Pereira | 601/7 |
| 6,527,783 | B1 | * | 3/2003  | Ignon | 606/131 |
| 6,535,761 | B2 | * | 3/2003  | Bernabei | 607/3 |

FOREIGN PATENT DOCUMENTS

| EP | 0 625 360 | 11/1994 |
| GB | 1077143 | 7/1967 |
| WO | WO 00/02620 | 1/2000 |
| WO | WO 02/49717 | 6/2002 |

* cited by examiner

Primary Examiner—Mark Bockelman
(74) Attorney, Agent, or Firm—Foley & Lardner

(57) ABSTRACT

Application of electrical pulses and mechanical vibrations to the skin is provided in a controlled manner, in order to increase the absorption of substances applied previously on the skin. A dermabrasion treatment is first performed on a region of the skin to be later given a skin absorption enhancement treatment. After the dermabrasion treatment, electrical pulses are provided to the skin by way of an array of electrodes disposed on a vibrating head, and the mechanical vibrations are provided to the skin by way of the vibrating head being made to vibrate. Preferably, the electrical and mechanical vibrations are at the same frequency and phase with respect to each other, in order to increase the absorption effect. Also, a suction may be applied to the skin, in order to provide for a substantially uniform absorption of the substance that was applied previously on the skin.

9 Claims, 6 Drawing Sheets

METHOD AND APPARATUS FOR SKIN ABSORPTION ENHANCEMENT AND CELLULITE REDUCTION

CROSS-REFERENCE TO RELATED PATENT APPLICATIONS

This application claims priority to U.S. Provisional Application No. 60/281,808, filed Apr. 6, 2001, and is a continuation-in-part of U.S. patent application Ser. No. 09/942,044, filed Aug. 30, 2001, which is in turn a continuation-in-part of U.S. patent application Ser. No. 09/922,927, filed Aug. 7, 2001 now U.S. Pat. No. 6,535,761, each of which is incorporated in their entirety herein by reference.

BACKGROUND OF THE INVENTION

A. Field of the Invention

The invention relates to application of both electrical pulses and mechanical vibrations to the skin at the same time in a controlled manner, along with an optional application of a vacuum in order to achieve a suction affect to the skin, in order to increase the absorption of a substance applied previously on the skin as well as to provide for a substantially uniform absorption of the substance (such as collagen) previously applied to the skin.

B. Description of the Related Art

It is known that a mechanical vibration applied to the skin is useful in order to increase the absorption of a substance previously applied to the skin. Such a substance may be a liquid, a gel, a lotion, or a cream, for example.

It is desired to provide an apparatus and a method to increase the absorption of a substance previously applied to the skin, in order to obtain an increased (e.g., moisturizing) affect of the substance applied to the skin.

SUMMARY OF THE INVENTION

The present invention is directed to an apparatus and a method for enhancing the absorption of the skin of substances previously applied on the skin.

To accomplish this, the present invention uses a sequence of electrical pulses (between 20 and 200V peak to peak, preferably, and between 50 and 15,000 Hz preferably) provided to electrodes that are placed in contact with the skin (with the substance provided between the electrodes and the skin). There is also provided a corresponding surface vibration to the skin, by application of a mechanical vibration to the skin. The mechanical vibration is preferably of the same frequency and phase as the electrical pulses applied to the skin. The mechanical vibration is provided by way of a vibrating plate that also contains the electrodes (which provide the electrical stimulus to the skin at the same time the mechanical vibration is provided to the skin).

The substance to be absorbed by the skin is applied between the skin and the plate. Such a substance may be a cream, liquid or gel (for example, collagen, or cocoa butter, or suntan oil, or other types of skin enhancement lotions).

The method according to the invention includes:

1) The application of a liquid, a gel, a lotion, or a cream on the skin.
2) An apparatus which includes the following elements to perform the preceding treatment:
   a) a vibrating plate.
   b) an array of electrodes on the plate.
   c) a pulse generator connected to the array of electrodes.
3) The application on the skin of the apparatus in order to enhance the natural absorption of the substance previously provided on the skin.

BRIEF DESCRIPTION OF THE DRAWINGS

The foregoing advantages and features of the invention will become apparent upon reference to the following detailed description and the accompanying drawings, of which.

DETAILED DESCRIPTION OF THE PREFERRED EMBODIMENTS

Preferred embodiments of the invention will be described in detail below, with reference to the accompanying drawings.

Based on experimental tests on the skin, it has been found by the inventor that after one or more pulses are applied between two points on the skin, transpiration (or absorption)

in the area between the two points on the skin increases. The pulses that give optimal results are exponential pulses that are generated by a charged capacitor discharged on two points on the skin.

These experimental results have been utilized by the inventor in order to develop an apparatus and method that maintains the transpiration of the skin at a high level, so that the skin can readily absorb a gel, liquid, lotion, or cream previously applied to the skin.

Figure 2A:
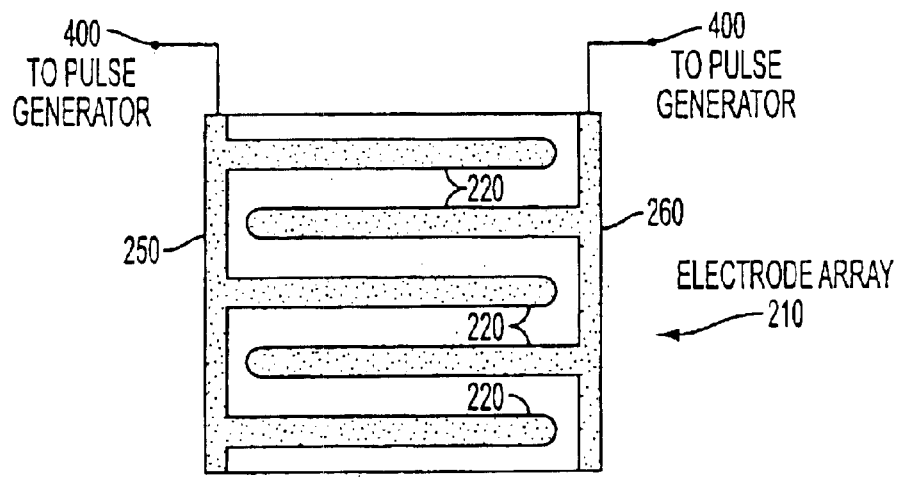
FIG. 2A shows an array of electrodes provided on an outer surface of the vibration plate that faces the skin, according to a first embodiment of the invention.
Figure 2B:
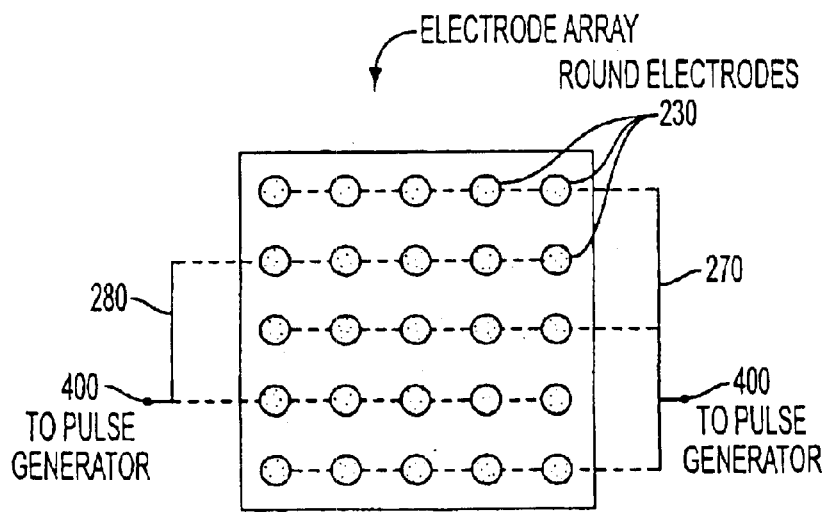
FIG. 2B shows an array of electrodes provided on an outer surface of the vibration plate that faces the skin, according to a second embodiment of the invention.
Figure 4:
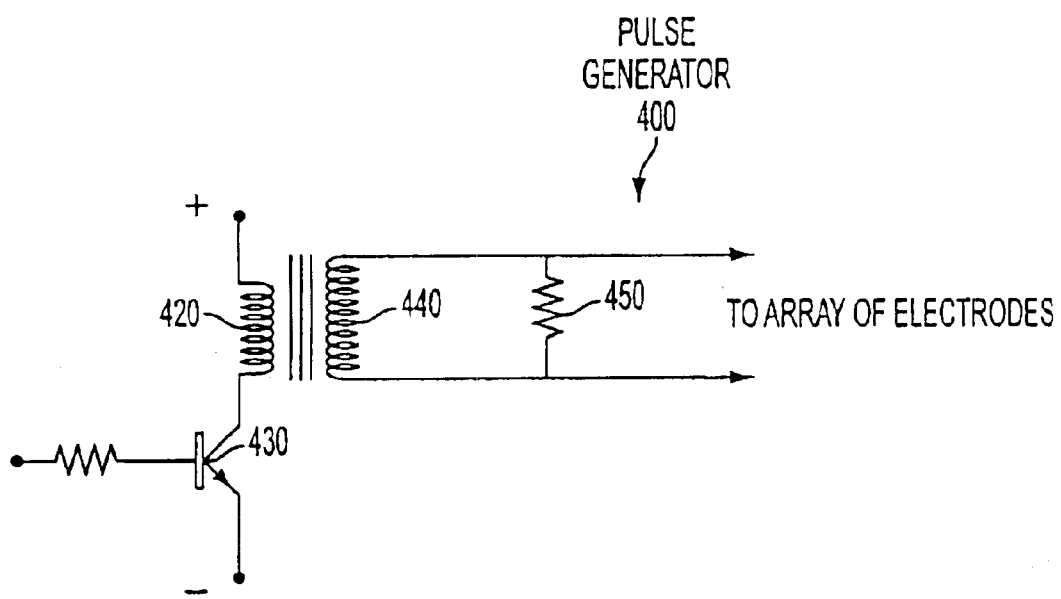
FIG. 4 shows an electrical diagram of a pulse generator that provides electrical pulses to an array of electrodes disposed on a vibrating plate provided at a head-end of the probe, according to one possible configuration of an apparatus according to the invention.
Figure 5:
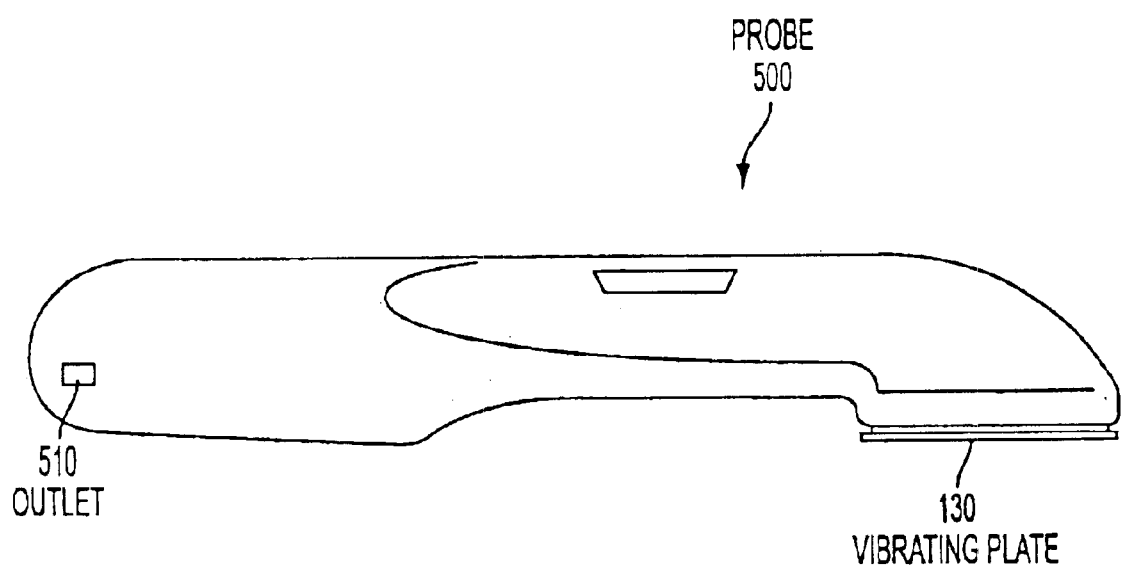
FIG. 5 shows one configuration of a hand-held probe that is used to provide both electrical and mechanical stimulation to the skin, according to the invention.

The apparatus according to the present invention applies a sequence of pulses over an area or skin, by using an array of electrodes that are placed in contact with the skin. The array of electrodes are provided on a vibrating plate at the head of a probe, such as a hand-held probe 500 as shown in FIG. 5. The array of electrodes may be a configured as shown in FIG. 2A in a first embodiment, whereby odd rows of electrodes are electrically connected to each other, and thereby to a pulse generator 400 (see also FIG. 4) via a first electrical connection. The even rows of electrodes are electrically connected to each other, and also to the pulse generator 400 via a second electrical connection. The array of electrodes on the vibrating plate may alternatively be configured as shown in FIG. 2B in a second embodiment, whereby odd rows of round electrodes are electrically connected to each other, and thereby to the pulse generator 400 via a first electrical connection. The even rows of round electrodes are electrically connected to each other, and thereby to the pulse generator 400 via a second electrical connection.

The increase of the transpiration of the skin that is obtained by way of the present invention has the effect of increasing the absorption of liquids, creams, lotions, or gels that have been previously provided on the skin in the area between where the electrodes are applied to the skin.

The electrical pulses that are applied on the skin in order to enhance the transpiration of the skin are pulses obtained by a discharge of a capacitor on the skin. A square-wave pulse input to a primary winding of the transformer 410 of FIG. 4, with an output of the secondary winding of the transformer 410 being coupled to the skin, provides the same effect as a discharging capacitor. The exponential pulses are generated during the rising edge and falling edge of each square-wave input pulse, and have opposite sign (positive for the rising edge, negative for the falling edge). With the use of such a pulse generator as shown in FIG. 4, it is possible to apply a burst of separate pulses (e.g., around 1000 per second) to the skin, which provides a transpiration effect better than just providing one pulse to the skin.

Normally, when a square wave is applied to the skin, due to the capacitive effect of the skin, it is possible to obtain about a three microsecond time constant exponential delay current. This is what happens when a square wave voltage is applied to a circuit that corresponds to a resistor in parallel with a capacitor.

With such a circuit, only the peak current is enhanced, charging to a maximum allowable voltage the skin capacitance by applying an electrical energy equal to the magnetic energy of the transformer 410. This effect most like provides for the opening of the cell membranes of the skin (to achieve the transpiration effect) only during the time when each pulse is applied to the skin.

The effect of applying the probe to the skin is that the skin vibrates due to the electrical pulses applied by way of the array of electrodes. The electrical pulses are preferably applied at a fixed frequency between 200 and 10,000 Hz (optimally at a frequency value between 2,500 to 3,000 Hz), and are grouped in a burst. The ON time of each burst is a fixed value between 5 to 50 milliseconds, and the OFF time between two consecutive bursts is a fixed value between 5 to 50 milliseconds (the preferred burst ON time is 10 milliseconds and the preferred OFF time between consecutive bursts is 10 milliseconds).

As described above, the electrical pulses applied to the skin by way of the electrodes are preferably exponential pulses with peak-to-peak voltage of 160 V at a fixed frequency between 2,500 to 3,000 Hz. One way of providing such electrical pulses is by an electrical structure that corresponds to a pulse generator 400 as shown in FIG. 4, in which a transformer 410 is used as an element.

The transformer 410, as well as the other elements of the pulse generator 400, are preferably housed within the probe 500 of FIG. 5.

Referring back to FIG. 4, the primary winding 420 of the transformer 410 is driven by a transistor 430 that is switched on and off, and the secondary winding 440 of the transformer 410 is directly applied to the array of electrodes (see FIG. 1A or 1B) with an electrical resistance 450 provided therebetween. The electrical resistance 450 may be 200 Kohm or some value in that range (e.g., 100 Kohm to 500 Kohm), and is provided in order to avoid high voltages when the array of electrodes are not applied to the skin, so that in that case it operates as an open circuit. In such a situation, the peak-to-peak voltage is 400 V or thereabouts.

As described above, along with the electrical pulses applied to the skin, a mechanical vibration is also provided to the skin in order to increase the absorption of a substance previously applied on the skin.

The absorption effect is enhanced by the simultaneous increase of transpiration, whereby the absorption effect is greatest when the mechanical vibration is synchronized in phase and in frequency with the electric pulse application. Thus, in the example discussed above, while the electrical burst of pulses (at 2,200 Hz) are provided to the skin at a burst ON/OFF frequency, e.g., 50 Hz, by way of an electrode array, the skin is also mechanically vibrated at the same frequency, e.g., 50 Hz, by way of the vibrating plate. The mechanical vibration and the electrical burst application are also preferably provided in phase with respect to each other, in order to increase the skin absorption effect. There are several well known ways to achieve this frequency and phase synchronization. In the preferred embodiments described herein, an optical sensor (not shown) detects the movement of the eccentric of the motor, and gates the burst of electrical pulses based own the detected movement.

Thus, in the example discussed above, while the burst of electrical pulses are provided to the skin by way of the electrode array, the skin is also mechanically vibrated at the same frequency by way of the vibrating plate. The mechanical vibration and electrical pulse application is also preferably provided in phase with respect to each other, in order to increase the skin absorption effect.

Moreover, the absorption effect is further enhanced when the mechanical vibration is applied orthogonal to the surface of the skin. An explanation of the physical phenomena of the present invention is that, while the electrical pulses "stretch" the skin, thus increasing periodically the diameter of the pores of the skin, at the same time the mechanical vibration "pumps" the substances (gel, liquid or cream) inside the skin (through the opened pores). The mechanical and electrical synchronization achieves the effect that the "pumping" action (due to the mechanical stimulation of the skin) takes place at the same instant in time that the pores are at their maximum "open" diameter (due to the electrical stimulation of the skin).

The apparatus according to the present invention includes two main parts:
A) a handle containing a power source (e.g., batteries) and a pulse generator; and
B) a vibrating head containing components for generating the vibration and also containing an array of electrodes.

Figures 1A, 1B:
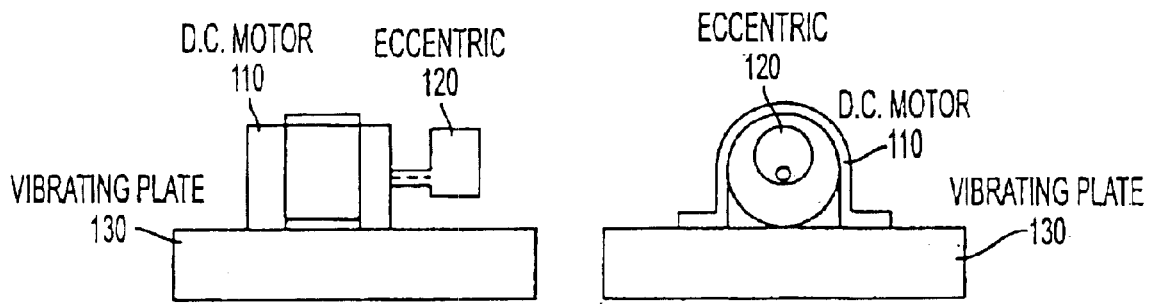
FIG. 1A is a side view of a vibration mechanism that is disposed within an apparatus according to the present invention.
FIG. 1B is a front view of the vibration mechanism of FIG. 1A.

The vibrating head, in the preferred configuration, includes a D.C. electrical motor for generating vibrations to the skin. FIGS. 1A and 1B show two different views of the D.C. electrical motor 110, the rotating shaft of the D.C. electrical motor 110 is an eccentric 120 to thereby provide eccentric motion. The eccentric motion, during rotation of the D.C. electrical motor 110, generates a vibration onto the vibrating plate 130 (that is directly coupled to the D.C. electrical motor 110) that is at the same frequency of the rotation of the D.C. electrical motor 110 (e.g., 50 Hz or 60 Hz or some other desired frequency).

As explained earlier, FIG. 4 shows circuitry for providing electrical pulses to the array of electrodes shown in FIGS. 2A and 2B. The circuitry of FIG. 4 corresponds to a pulse generator 400, and is preferably disposed within the housing of the probe 500 of FIG. 5. The electrical pulses generated by the pulse generator 400, when those pulses are provided to the skin, preferably are sinusoidal pulses with peak-to-peak voltage of 160 V at a frequency of between 2,500 Hz to 3,000 Hz. Of course, other peak-to-peak voltage values (e.g., 100 V to 200 V) and operating frequencies (50 Hz to 15,000 Hz) may be employed, while remaining within the scope of the invention as described herein.

FIGS. 1A and 1B show the vibrating plate 130 that is physically coupled to the D.C. electrical motor 110. The vibrating plate 130 preferably is 50×50 mm in size, where parallel metallic stripes are deposited on it as shown in FIG. 2A, in order form the array of electrodes. The vibrating plate 130 is caused to vibrate at the same phase and frequency as the electrical pulses provided to the skin by way of the array of electrodes (disposed on the vibrating plate), in order to enhance the skin absorption effect.

As shown in FIG. 2A, which shows a first embodiment of an electrode array 210 that is provided on a skin-side surface of the vibrating plate 130, five parallel metallic stripes 220 are provided, each preferably of a size of 50 mm×4 mm. Each of the five electrodes 220 are preferably 6 mm apart from adjacently-positioned electrodes. The electrodes 220 are alternately electrically connected (e.g., the first, third and fifth row are electrically connected to each other by way of electrical line 250; and the second and fourth rows are electrically connected to each other by way of electrical line 260). Other electrode array configurations are possible while remaining within the scope of the invention, such having a number of electrodes greater than two, such as having seven or eight electrodes.

FIG. 2B shows a second embodiment of an electrode array that is provided on a skin-side surface of a vibration plate. In FIG. 2B, there are provided 25 round electrodes 230 each of 4 mm diameter, each separated at least 6 mm from adjacently-positioned round electrodes. The round electrodes 230 are alternately electrically connected to each other (e.g., the electrodes on the first, third and fifth rows are electrically connected to each other by way of electrical line 270; and the electrodes on the second and fourth rows are electrically connected to each other by way of electrical line 280). The spacing between the electrodes 230 shown in FIG. 2B may vary between 1 to 20 mm and the size of each of the electrodes 230 may vary between 1 to 20 mm in diameter.

Figure 2C:
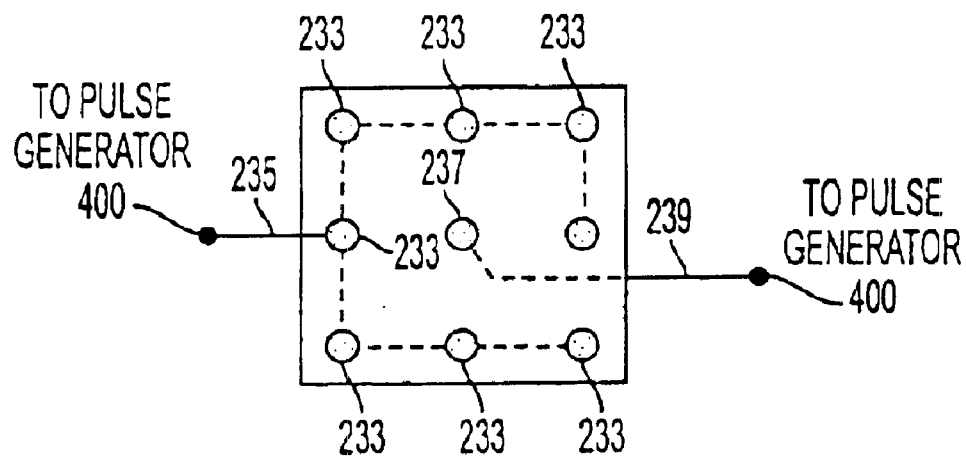
FIG. 2C shows an array of electrodes provided on an outer surface of the vibration plate that faces the skin, according to a third embodiment of the invention.

FIG. 2C shows an array of electrodes provided on an outer surface of the vibration plate that faces the skin, according to the third embodiment of the invention. In FIG. 2C, there are provided electrodes 233 that are disposed on the periphery of the vibration plate, which are electrically coupled to each other, and which are electrically coupled to the pulse generator 400 by way of a first electrical connection 235. In FIG. 2C, there is also provided a centrally-positioned electrode 237, which is not electrically coupled to any other of the electrodes, and which is electrically coupled to the pulse generator 400 by way of a second electrical connection 239.

Figure 3:
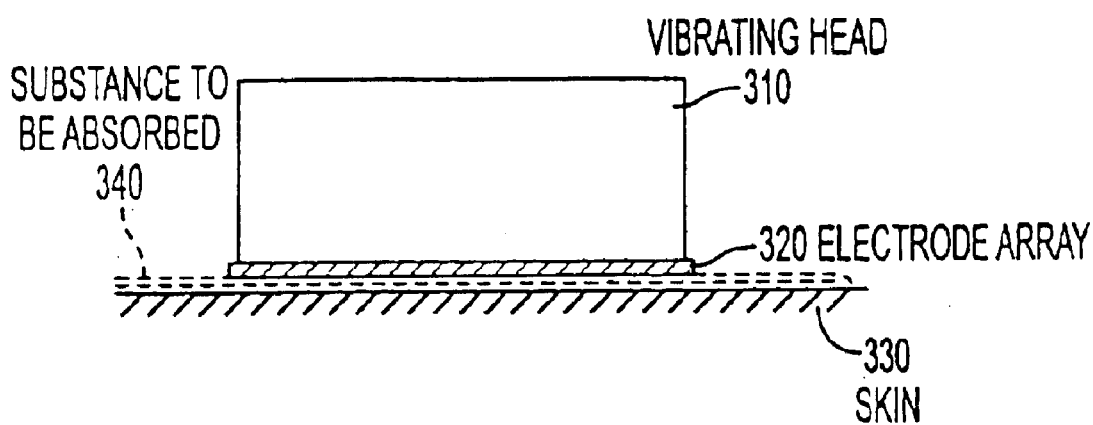
FIG. 3 shows a side view of a head of a probe that is used to provide both electrical and mechanical stimulation to the skin, in order to have a substance previously applied to the skin to be absorbed better, according to the invention.

FIG. 3 shows a side view of a vibrating head 310 of a probe that is used to provide both electrical and mechanical stimulation to the skin according to the present invention, in order to have a substance previously applied to the skin be absorbed better. As shown in FIG. 3, the vibrating head 310 includes the array of electrodes 320 provided on a skin-side surface thereof. The array of electrodes 320 may be provided in a manner such as shown in either FIG. 2A or 2B, for example. Between the array of electrodes 320 and the skin 330 there is provided a substance 340 to be absorbed, whereby the substance 340 has been previously applied to the skin 330 (e.g., applied to the skin between 30 seconds to 2 minutes before the probe is to be applied to the skin 330). Application of mechanical vibrations and electrical pulses enhances the absorption of the substance 340 into the skin 330.

FIG. 5 shows one configuration of a hand-held probe 500 that may be used to provide both electrical and mechanical stimulation to the skin, according to the invention. The probe 500 is configured to be readily held by one hand of a user. A bottom portion of the probe 500, at which a user's hand is gripped thereon to thereby hold the probe 500, may include an outlet 510 for coupling an electrical cable to an electrical outlet (e.g., wall outlet), so as to provide A.C. voltage to the probe 500 in that manner. Alternatively, battery power may be used, by way of batteries (not shown) disposed within the housing of the probe 500. Battery power may be utilized when A.C. power is not readily available. Also, the pulse generator 400 of FIG. 4 is preferably housed at the handle portion of the probe 500.

The head portion of the probe 500 is where the vibrating plate 130 (see FIG. 1A or 1B) is provided, and also where the D.C. electrical motor 110 (see also FIG. 1A or 1B) that provides the mechanical vibrations to the vibrating plate 130 is preferably provided housed within. The array of electrodes (see FIG. 2A or 2B) are provided on an outer surface of the vibrating plate 130, thereby facing the skin of a user to be treated with the probe 500.

A typical application time of the probe to the skin may be on the order to 10s of seconds up to several minutes.

Figure 6:
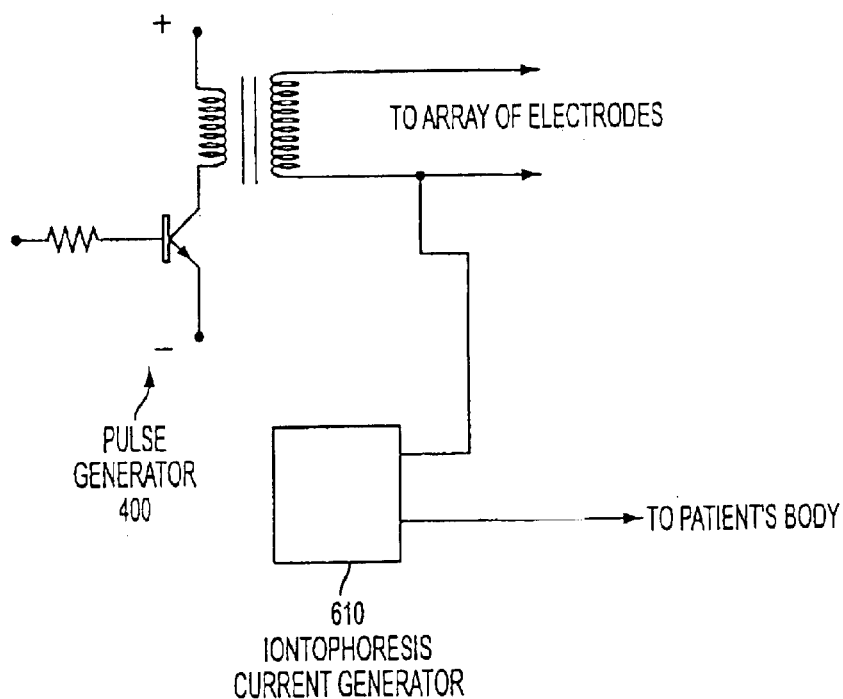
FIG. 6 shows a current generator connection according to a fourth embodiment of the invention.

In a fourth embodiment, as shown in FIG. 6, the output of the pulse generator 400 (see also FIG. 4) is connected to a D.C. current generator 610, which induces a iontophoresis effect in addition to the previously described skin absorption/transpiration effects. The iontophoresis effect is well known to those skilled in the art, and several iontophoresis electrical generators are currently available in the market, either D.C. or D.C. pulsed. A D.C. current output by the D.C. current generator 610 is applied between the electrodes of the probe and a ground plate that is connected with the patient's body. Depending on the substance to be absorbed into the patient's skin, the patient ground plate connection is coupled to either the positive or the negative of the D.C. current generator 610, in a manner known to those skilled in the art. Instead of using continuous D.C. current, there can alternatively be provided D.C. current pulses that have the same average current value as the continuous D.C. current case, and which have a duty cycle between 5 and 50% and a frequency between 10 and 5000 Hz. In such a case, the peak current of the D.C. current pulses is higher during the pulsed (ON) times.

Figure 7:
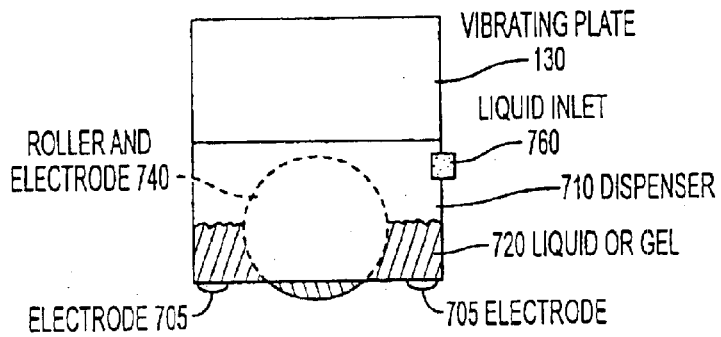
FIG. 7 shows elements provided at the head portion of a probe, according to a fifth embodiment of the invention.
Figure 8:
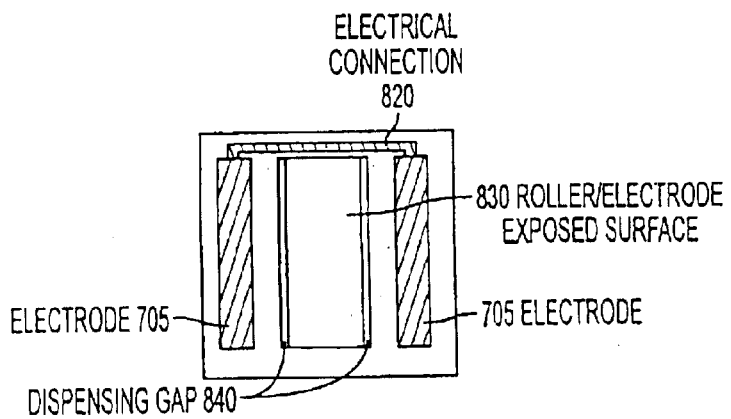
FIG. 8 shows a front view of the head portion of the probe according to the fifth embodiment of the invention.

In a fifth embodiment, as shown in FIGS. 7 and 8, a dispenser or chamber 710, which is configured to hold liquid or cream or gel 720, is integrated in the vibrating head of the probe. The dispenser or chamber 710 is provided between an array of electrodes 705 and the vibrating plate 130. The burst of electrical pulses are applied by way of a conductive roller 740 that dispenses the liquid, and by the array of electrodes 705. A D.C. current as in the third embodiment can also be added between the array of electrodes 705 and the patient's body, to induce a iontophoresis effect as well. While the vibrating head is moved on the patient's skin, the roller 740 delivers the liquid or cream or gel 720 to the patient's skin.

The chamber 710 in which the roller 740 is disposed in the vibrating head can be filled with a liquid, cream or gel substance 720 by way of a removable cap (not shown). In particular, the cap is removed (e.g., screwed off of the head of the probe), and then a user fills the chamber 710, through the liquid inlet 760, with the substance 720 to be provided to the patient's skin. The user then closes the cap (e.g., screws it back onto the liquid inlet 760) to thereby keep the substance 720 within the chamber 710 of the probe until it is ready to be applied to the patient's skin by way of the roller 740.

FIG. 8 shows a front view of the electrodes 705, which are shown as two stripe electrodes that are electrically connected to each other by way of electrical connection 820. Of course, other types of electrode arrays, such as those shown in FIGS. 2A and 2B, can alternatively be used in this fifth embodiment. The exposed surface 830 of the roller 740 that applies the substance to the patient's skin, is shown in FIG. 8. Dispensing gaps 840 are also shown in FIG. 8, whereby these gaps 840 allow the liquid, cream or gel substance 720 in the chamber 710 to gradually come out of the chamber 710 and thereby be applied to the patient's skin by way of the roller 740.

Figure 4A:
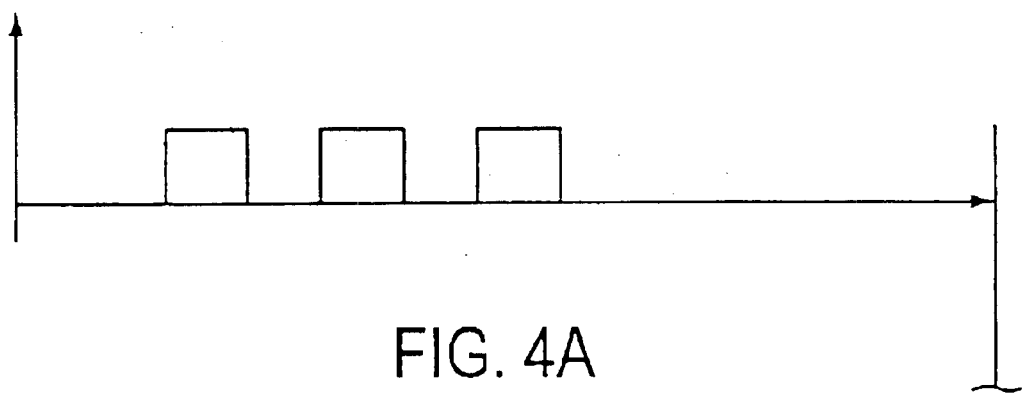
FIG. 4A shows a train of square-wave pulses that are input to the pulse generator of FIG. 4.
Figure 4B:
FIG. 4B shows a train of exponential pulses that are output from the pulse generator of FIG. 4.

In a sixth embodiment of the invention, an apparatus for enhancing absorption of the skin includes an array of electrodes, and a pulse generator that is electrically coupled to the array of electrodes. The disposition of the array of electrodes may be any of the dispositions shown in FIGS. 2A–2C, for example. In the sixth embodiment, electrical pulses outputted by the pulse generator 400 to the array of electrodes are a sequence of exponential pulses, such as the pulse train shown in FIG. 4B. The exponential electrical pulses are applied to the skin by way of the array of electrodes and are generated by the secondary winding of a high voltage transformer with the primary winding driven by a square wave voltage, as seen by FIGS. 4, 4A and 4B.

In the sixth embodiment, unlike the previous embodiments, a vibrating head is not utilized, but rather skin absorption enhancement is obtained just by the providing of the electrical pulses to the skin by way of the array of electrodes. The array of electrodes according to the sixth embodiment are provided on a plate at the head of the probe, whereby the head and the plate do not vibrate. Thus, in the sixth embodiment, the structure as shown in FIGS. 1A and 1B would not be utilized, but rather just a plate for holding the electrodes in place at the head of the probe would be needed.

In a seventh embodiment, a vibrating head is utilized, as in the first through fifth embodiments, but where the vibrating head is capable of being turned on or off, by way of a control (e.g., switch) provided on the probe. The control can readily be manipulated by an operator of the probe, in order to treat a patient.

Figure 9:
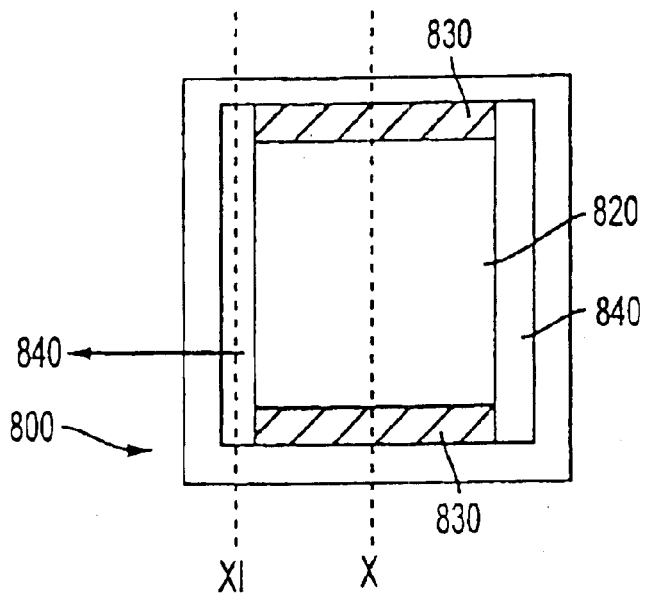
FIG. 9 shows a front view of the head portion of the probe according to an eighth embodiment of the invention.
Figure 10:
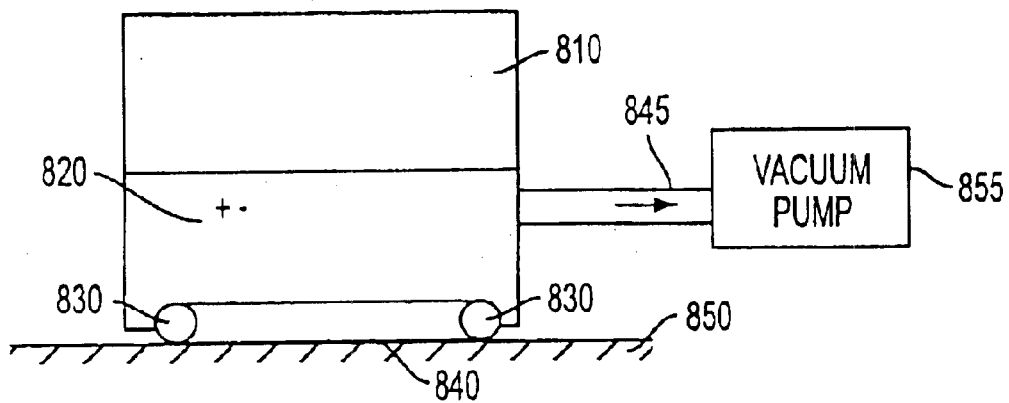
FIG. 10 shows a first section view of the head portion of the probe according to the eighth embodiment of the invention, whereby suction is not being applied to the skin.
Figure 11:
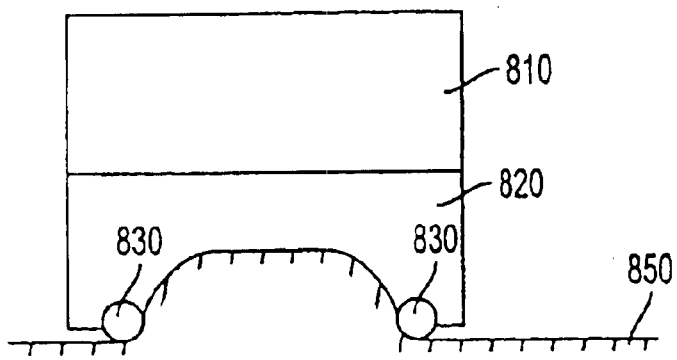
FIG. 11 shows a second section view of the head portion of the probe according to the eighth embodiment of the invention, in which suction is being applied to the skin.

An eighth embodiment of the invention is described below, with reference to FIGS. 9–11. FIG. 9 shows a front view of a head 800 of a probe, whereby that view shows the portion of the probe that is applied to the skin of a patient. FIG. 10 shows a section view taken along an axis of one belt, and FIG. 11 shows a section view taken at the middle of the head of the probe.

The eighth embodiment provides for a fairly even absorption under the skin of a substance previously applied to the skin, such as collagen previously applied to the skin. In the eighth embodiment, a head 800 of a probe to be applied to the skin includes a vibrating plate 810, a vacuum chamber 820, rollers 830, and belts 840 disposed around the rollers 830. The rollers 830 are conductive rollers, whereby the rollers 830 are electrically coupled to electrodes (see FIGS. 2A through 2C, for example) provided on the vibrating plate 810. As in the other embodiments, a pulse generator (see FIG. 4, for example) is electrically coupled to the electrodes on the vibrating plate 810, in order to provide electrical pulses to the patient's skin (by way of the conductive rollers).

In the eighth embodiment, the rollers 830 are separated from each other by around 40 mm. Of course, other separation distances are possible, while remaining within the scope of the invention (e.g., 20 mm to 80 mm separation). The rollers 830 are disposed at one end of the vacuum chamber 820, whereby the vacuum chamber 820 includes an opening that is coupled to a pipe 845 that is in turn coupled to a vacuum pump 855.

When the vacuum pump 855 is operated, the vacuum chamber 820 generates a suction effect on the skin 850, thereby enabling a stronger contact between the rollers 830 and the skin 850, and thereby generating an additional massaging effect to the skin 850, in addition to the vibrations generated by the vibrating plate 810. On opposite ends of the rollers 830 are the belts 840, which are preferably rubber belts. The belts 840 are used in order to avoid direct friction between the skin 850 and the body of the vacuum chamber 820.

The eighth embodiment provides good skin absorption results and decreases the appearance of cellulite on the skin after application of a substance for reducing cellulite is applied to the skin. Such a substance for reducing cellulite that can be applied to the skin may be jarulon acid, for example. Such a substance could also be previously spread on the skin and absorbed by the skin utilizing one of the previously-described embodiments.

Also, while the eighth embodiment has been described as having a vibrating plate, as in the first through fifth embodiments, a non-vibrating plate as in the sixth and seventh embodiments (when the vibrating plate is turned off) may be utilized in an alternative configuration. In that case, the plate disposed above the vacuum chamber is non-vibrating, and contains electrodes disposed therein.

Experimental results of the application of the several embodiments of the skin absorption apparatus described hereinabove to the skin demontrated that a noticeable variation of results and rate of absorption of substances occurred. The analysis was carried out over an area of skin previously dermabraded with a standard microdermabrader available on the market and an adjacent area not previously dermabraded. This analysis demostrated that the results obtained in the dermabraded area are fairly constant and reproducible while the results in the non-dermabraded area are variable and somewhat inconsistent. This inconsistency is due to the fact that the stratum corneum (also referred to as the horny or dead outermost layer of the epidermis) of the skin acts like a barrier to the absorption of the substances applied to the skin, and moreover it increases the electrical resistance of the skin, thereby somewhat decreasing the absorption effect of the skin absorption treatment according to the invention.

The thickness of the stratum corneum is variable from person to person, and moreover it is variable from time to time in the same person. This induces a variability that makes it difficult to come up with a standard application time of the skin absorption apparatus according to the various embodiments of the invention. For this reason, according to yet another embodiment of the invention, a skin absorption treatment method includes a microdermabrasion performed before the application of the skin absorption apparatus in order to give more reproducible and more constant results as compared to the embodiments in which a microdermabrasion is not first performed. The microdermabrasion to be performed prior to the skin absorption treatment may be one described in various U.S. patents assigned to Mattioli Engineering, Ltd., such as U.S. Pat. Nos. 6,322,568 and 6,039,745, each of which are incorporated in their entirety herein by reference, or other types of dermabrasion treatments conventionally known.

Preferably, the dermabrasion treatment is performed for 3 minutes in order to remove 100 micron of the corneum status of the skin in an area to be later treated with a skin absorption enhancement device according to one of the embodiments of the invention. Ideally, the skin absorption treatment is performed soon after (e.g., within 5 minutes) of the completion of the dermabrasion treatment. Of course, other time lengths of dermbrasion treatment, depth of corneum status removal, and time between the dermabrasion treatment and the skin absorption treatment, may be contemplated while remaining within the scope of the invention as described herewinabove.

Different embodiments of the present invention have been described according to the present invention. Many modifications and variations may be made to the techniques and structures described and illustrated herein without departing from the spirit and scope of the invention. Accordingly, it should be understood that the apparatuses described herein are illustrative only and are not limiting upon the scope of the invention.

What is claimed is:

1. A treatment method for enhancing absorption of substances provided on a skin surface of a patient, comprising:
   a) applying a dermabrasion treatment to a region of the skin surface by way of a dermabrasion apparatus;
   b) thereafter, applying a substance to the skin that is intended to be absorbed within the skin;
   c) applying a vibration to the skin of between 10 to 200 Hz, the vibration being provided by way of a vibrating plate that is placed on the skin, the vibrating plate being disposed on a hand-held probe; and
   d) applying a sequence of bursts of electrical pulses at a frequency between 50 to 15,000 Hz and peak voltage between 20 and 200 V to an array of electrodes that are placed on the skin, the array of electrodes being disposed on the vibrating plate,
   wherein the sequence of bursts of electrical pulses and the vibration are provided to the skin at a same time in order to enhance absorption of the substance applied to the skin.

2. The treatment method according to claim 1, further comprising:
   e) applying a vacuum to the skin when performing steps b) and c), in order to provide a substantially uniform absorption of the substance within the skin.

3. The treatment method according to claim 1, wherein the electrodes are parallel metallic stripes that are alternately connected to each other and that are provided on an outer surface of the vibrating plate.

4. The treatment method according to claim 1, wherein the electrodes are round electrodes alternately electrically connected to each other and that are provided on an outer surface of the vibrating plate.

5. The treatment method according to claim 1, wherein a D.C. current is applied between the electrodes and a ground plate connected to the patient.

6. The treatment method according to claim 1, wherein the applying step b) is accomplished by dispensing of liquid or gel or cream or lotion by way of a roller integrated in the probe.

7. The treatment method according to claim 6, wherein a D.C. current is applied between the electrodes and a plate connected to the patient.

8. A method for reducing cellulite on skin, comprising:
   a) applying a dermabrasion treatment to a region of the skin;
   b) thereafter, applying mechanical vibrations to the region of the skin by way of a probe;
   c) applying electrical pulses to the region of the skin, by way of the probe, at a same time the mechanical pulses are applied to the region of the skin in step b); and
   d) concurrently with steps b) and c), generating a suction at the probe to suck at least a portion of the region of the skin towards the probe while the probe is being moved along the region of the skin.

9. The method according to claim 8, further comprising:
   between steps a) and b), applying a cellulite-reducing substance to the skin,
   wherein the vibrating applying step enhances absorption of the substance within the skin, and
   wherein the suction generating step evenly distributes the substance within the skin.

* * * * *